United States Patent [19]

Richardson

[11] Patent Number: 5,717,005
[45] Date of Patent: Feb. 10, 1998

[54] ADHESIVE COMPOSITIONS AND PRODUCTS

[75] Inventor: Mark Christopher Richardson, Huby, United Kingdom

[73] Assignee: Smith & Nephew PLC, London, United Kingdom

[21] Appl. No.: 167,914

[22] PCT Filed: Jun. 19, 1992

[86] PCT No.: PCT/GB92/01112

§ 371 Date: Dec. 20, 1993

§ 102(e) Date: Dec. 20, 1993

[87] PCT Pub. No.: WO93/00118

PCT Pub. Date: Jan. 7, 1993

[30] Foreign Application Priority Data

Jun. 21, 1991 [GB] United Kingdom .................. 9113448

[51] Int. Cl.$^6$ .............................. A61L 15/03; A61F 13/00
[52] U.S. Cl. .......................... 523/111; 523/118; 604/307; 424/448; 514/635; 514/772.4; 528/905; 602/48; 602/52; 602/54
[58] Field of Search .................... 523/111, 118; 424/448; 514/635, 772.4; 602/48, 52, 54; 604/307; 528/905

[56] References Cited

U.S. PATENT DOCUMENTS 5,035,687  7/1991  Sandbank ................... 602/52

FOREIGN PATENT DOCUMENTS

| 0011471 | 5/1980 | European Pat. Off. . |
| 0023395 | 2/1981 | European Pat. Off. . |
| 0065370 | 12/1982 | European Pat. Off. . |
| 0065399 | 12/1982 | European Pat. Off. . |
| 2186486 | 8/1987 | European Pat. Off. . |
| 0240097 | 10/1987 | European Pat. Off. . |
| 0256893 | 2/1988 | European Pat. Off. . |
| 9000066 | 1/1990 | WIPO ....................... 602/54 |

OTHER PUBLICATIONS

World Patents Index (Latest), Week 9016, AN=90–121106, Derwent Publications Ltd., London, GB & JP.A2073013, 13 Mar. 1990.

*Primary Examiner*—Andrew E C Merriam
*Attorney, Agent, or Firm*—Larson & Taylor

[57] ABSTRACT

Chlorhexidine gluconate-containing adhesives have dispersed therein solid chlorhexidiene particles which will pass through a 125 µm sieve and at least about 30% of the total volume of particles has a size of not less than 5 µm. The adhesive may be a vinyl ether adhesive and may be coated upon a backing layer such as a hydrophilic polyurethane to produce products suitable for use as wound dressings, IV dressing or incise drapes. The chlorhexidine gluconate may be obtained as a freeze-dried solid and added directly, in suspension, to the adhesive mass without further milling.

11 Claims, No Drawings

ADHESIVE COMPOSITIONS AND PRODUCTS

This invention relates to adhesive compositions and to adhesive products. More particularly, the invention relates to medicated adhesive compositions and to products coated therewith.

Adhesive products containing a releasable medicament in the adhesive are known. The advantage of having a medicament, such as an anti-bacterial agent, in the adhesive is that the medicament is delivered to the site for release and use when the adhesive is applied eg. as part of a wound dressing. By providing a vehicle from which such medicaments as anti-bacterial agents can be released in a sustained manner, the area can be maintained free from bacterial infection. A known medicated adhesive product containing an antibacterial agent is sold under the trade name "OpSite CH" By T. J. Smith and Nephew Limited. The antibacterial incorporated into the adhesive layer is chlorhexidine acetate.

Chlorhexidine gluconate is also a well known antibacterial agent. However, because it is a extremely hygroscopic material its use is limited and in many applications it can only be used as a 20% aqueous solution, which is commercially available. In our researches we have found that it has only been possible to use gluconate solutions in adhesive formulations in amounts not exceeding about 3% by weight of chlorhexidine gluconate since at levels much above this the tack properties of the adhesive are adversely affected.

We have now found it possible to prepare chlorhexidine gluconate-containing adhesive compositions having higher levels of anti-bacterial activity and acceptable adhesive values then has been hitherto available.

Thus in accordance with the invention, there is provided an adhesive composition, suitable for medical applications, comprising an adhesive having dispersed therein solid particles of chlorhexidine gluconate, wherein said particles have a particle size of less than 125 µm and at least about 30% by volume of the particles have a particle size of not less than 5 µm.

Particles used in the invention which have a particle size of less than 125 µm are particles which will pass through a 125 µm mesh screen.

The solid form of chlorhexidine gluconate may be obtained by freeze-drying aqueous solutions of the gluconate, eg the commercially available 20% aqueous solution. The particle size of the freeze dried material is usually of a suitable size that the material requires no further comminution prior to incorporation into the adhesive mass.

The adhesives used in the invention may be any of those medically acceptable adhesives which are compatable with the gluconate. In particular the adhesive material should not contain groupings, such as free acid groups, which will react with the gluconate and thus render it unavailable for release. Suitably, the adhesive is one which is hydrophilic in nature.

Apt adhesives for use in the adhesive composition of the invention may include acrylic adhesives and adhesives based on polyvinyl ethers. A preferred acrylic adhesive is described in European Patent Publication No. 35399. A typical polyvinyl ether adhesive composition suitable for use in the present invention is that described as adhesive composition A in UK Patent specification No. 1280631.

The amount of chlorhexidine gluconate that is present in the adhesive can range up to 10% by weight of the weight of the composition without adversely affecting the tack of the adhesive. Thus amounts of chlorhexidine gluconate can be included which would exhibit bactericidal properties as well as bacteriostatic properties. Hitherto it has not been possible to include more than about 3% by weight chlorhexidine gluconate, as an aqueous solution, before the adhesive surface becomes deadened. At such low levels the anti-bacterial activity is restricted to that of bacteriostatic activity and with such adhesive compositions little or no bactericidal activity is observed.

We have also found that, on a weight for weight basis, adhesives based on solid gluconate have superior antibacterial properties than those adhesives based on chlorhexidine gluconate in solution. Effective bactericidal activity can be achieved at concentrations of from 2–3% by weight.

In accordance with a further aspect of the invention there is provided a process for the production of an adhesive composition which comprises admixing particles of chlorhexidine gluconate with a medically acceptable adhesive wherein the particles have a particle size of less than 125 µm and wherein at least about 30% by volume of the particles have a particle size of not less than 5 µm.

In a preferred embodiment of the process of the invention, freeze dried particles of chlorhexidine gluconate are dispersed in a liquid which is a non-solvent for the gluconate but a solvent for the adhesive. The liquid may suitably be a non-polar liquid. Thus for a composition base on a polyvinyl ether adhesive, a suitable solvent for the adhesive, which is a non-solvent for chlorhexidine gluconate is petroleum ether, commercially available is SBP2.

Dispersion of the particles can be achieved by conventional mixing techniques such as high shear mixing. After formation of the dispersion with the as-produced freeze dried chlorhexidine gluconate, the dispersion may be filtered through a suitably sized mesh screen and the particles caught on the screen recycled to the mixing zone.

We have found that by the choice of relatively large sizes of particles, good adhesion values can be retained and yet good release properties of the antibacterial can be achieved. If any significant comminution of the as-produced freeze dried product takes place, the adhesive properties of the composition are adversely affected.

The adhesive compositions of the invention are suitable for use in the manufacture of adhesive products such as wound dressings, intra-venous access site dressings (IV dressings) and surgical drapes.

Thus in accordance with another aspect of the present invention there is provided an adhesive product comprising a backing layer having coating thereon of a medically acceptable adhesive having dispersed therein solid particles of chlorhexidine gluconate, wherein said particles have a particle size of less than 125 µm and at least about 30% by volume of the particles have a particle size of not less than 5 µm.

The backing layer employed in the adhesive products of the present invention are desirably capable of conforming to the body contours when applied to the skin and should be flexible enough to move with the body without becoming detached. Suitable flexible backing materials include knitted, woven or non-woven fabrics, nets, microporous films such as plasticised polyvinyl chloride films, polymer blend films containing voids, polymeric films, including thermoplastic polyurethane and hydrophilic polyurethane, elastomeric polyesters, styrene-butadiene block copolymers such as Kraton (Trade mark) thermoplastic rubbers.

Favored materials which may be used at the backing layer in the adhesive product of the present invention include films of hydrophilic polymers. Apt hydrophilic polymers include hydrophilic polyurethanes, polyvinyl pyrrolidone, polyvinyl alcohol and cellulosic derivatives.

A favored hydrophilic polymer is a hydrophilic polyurethane. Suitable hydrophilic polyurethanes include those having the composition and prepared by the process described in British Patent No. 2093190B. The most suitable hydrophilic polyurethanes are those which contain from 5 to 50% by weight of water when hydrated, more suitably from 10 to 40% by weight of water and which have a thickness when present in a dressing of from 25 to 120 μm, more suitably 30 to 60 μm. A preferred film of hydrophilic polyurethane has a water content when hydrated of 20 to 30% for example 25% and a thickness of up to 50 μm for example 30 μm.

A favored flexible backing material is a microporous plasticised polyvinyl chloride film formed by the process disclosed in British Patent No. 884232. preferred microporous plasticised polyvinyl chloride films have a thickness of from 100 to 300 μm typically between 150 μm and 250 μm for example about 200 μm.

A further favored backing layer is a film of thermoplastic polyurethane including the linear polyester polyurethanes or polyether polyurethanes known as Estanes (Trade mark). Such polyurethanes are used as films from 15 to 75 μm in thickness, more favorably 20 to 35 μm in thickness for example about 25 μm or 30 μm.

The adhesive layer may vary in thickness depending upon the type of skin lesion, wound or other similar use the dressing is to be put, that is thinner layers up to about 5 mm may be used on non-exuding wounds or on dressings for use at intravenous sites while thicker layers for example up to 25 mm may be used on exuding wounds where the absorptive properties of the adhesive may be advantageously used.

The adhesive products of the present invention may be prepared by casting the backing layer from a solution of the appropriate polymer at a suitable concentration onto a silicone release paper and removing the solvent to give a film of the required thickness. A film of the adhesive composition at the required thickness is prepared and the two films brought together and adhered to each other to form a laminate, preferably without the use of any further adhesives. Handles may be applied at any convenient stage during the production of the dressing. Release coated protectors may be placed over the adhesive layer or layers and the laminate cut into dressings of the appropriate size for example 5 cm×5 cm, 7.5 cm×7.5 cm, 8 cm×8 cm, 10 cm×10 cm, 5 cm×10 cm and 10 cm×20 cm. The adhesive products, when used as wound dressings, for example, may be packaged in a bacteria-proof and water-proof pouch and be sterilized by conventional methods such as irradiation and ethylene oxide.

In use the sterile dressing is removed from the pouch, the protector removed from the adhesive surface of the dressing and the dressing is applied to the wound.

Dressings in accordance with the invention may be used as a dressing for wounds caused by physical or surgical trauma, burns, ulcers and the like, as a surgical drape, as dressing for intravenous access sites and any dressing for which long term attachment to the skin may be required.

In a further aspect therefore the present invention provides a method of treating a wound on an animal body by applying to the wound an adhesive dressing as hereinbefore described.

By a suitable choice of adhesive and/or backing layer, the adhesive products of the invention may be rendered impervious to water, yet will allow moisture vapor to pass therethrough. The rate at which moisture vapor passes through the dressing is the moisture vapor transmission rate (MVTR). The MVTR can be determined either with water in contact with the dressing (the 'inverted MVTR') or in contact with water vapor alone ('upright MVTR').

A suitable method of determining the upright moisture vapor transmission rate of the dressing of this invention is as follows. Discs of material under test are clamped over Payne Permeability Cups (flanged metal cups) using sealing rings and screw clamps. The exposed surface area of the test sample may be conveniently 10 cm². Each cup contains approximately 10 ml of distilled water. After weighing the cups are placed in a fan assisted electric oven maintained at 37±1° C. The relative humidity within the oven is maintained at 10% by placing 1 Kg of anhydrous 3–8 mesh calcium chloride on the floor of the oven. The cups are removed after 24 hours, allowed to cool for 20 minutes and re-weighed. The MVTR of the test material is calculated from the weight loss expressed in units of grams of weight per square meter per 24 hours.

A suitable method of determining the inverted moisture vapor transmission rate of the dressing of this invention is as follows. The method described above is employed except that the Payne Cups are inverted in the oven so that the water within the cups is in contact with the test material and in this case with the adhesive.

Aptly adhesive products in accordance with the present invention will have MVTR's in excess of 300 gm$^{-2}$ and preferably greater than 500 gm$^{-2}$, suitably more than 1200 gm$^{-2}$. Inverted MVTR's are preferably greater than upright MVTR's and are desirably greater than about 1200 gm$^{-2}$.

In a preferred aspect therefore the present invention provides an adhesive product in the form of a wound dressing which includes backing material comprising a hydrophilic polyurethane and a continuous layer of pressure sensitive adhesive comprising an adhesive composition in accordance with the invention and the product has a moisture vapor transmission rate of between 1400 and 1600 gm$^{-2}$ 24h$^{-1}$ at 37° C. and 100 to 10% relative humidity difference when the adhesive is in contact with moisture vapor.

The present invention will be illustrated by the following example.

A slurry was prepared of freeze dried chlorhexidine gluconate in petroleum ether (SBP2) using a high shear mixer. The concentration of the chlorhexidine gluconate was 12.5% w/w.

A portion of the slurry was then pumped to a SUSSMEYER Bead Mill comprising a 1.5 liter stainless steel shell filled with up to 99% volume of 1 mm diameter lead-free glass beads. The milled slurry was passed through a 125 μm sieve to remove any unmilled gluconate and any broken glass particles. Particle size distribution analysis showed that almost all the particles were below 16 μm with 48% in the range 2–4 μm.

A further portion of the slurry was passed directly through the 125 μm mesh sieve, without milling. Particle size analysis of this portion showed that, again most of the particles were below 16 μm. However a number of particles were found in the 16 to 100 μm range.

A vinyl ether adhesive was made as described for Composition A in UK Patent Specification No. 1280631.

To one part of the adhesive was added the screened slurry of milled chlorhexidine gluconate to a concentration of 5.3% by weight and to another part of the adhesive was added the screened slurry of the unmilled gluconate, again at a chlorhexidine gluconate concentration of 5.3%.

A third part of the adhesive was retained as a control and contained no added chlorhexidine gluconate.

Each of the three adhesives were cast onto a 25 μm thick polyurethane film at a coating weight of 30 gm$^{-2}$ Samples of each of the coated films were then subjected to ethylene oxide sterilisation and thereafter tested for microbiological activity by the IOBAN zone diffusion test against *Staphloccocus aureus* 10788 in comparison with non-sterilized samples of each coated film. The bacterial counts were made initially (0 mins) and after the lapse of 5 minutes. The results of the IOBAN tests are reported below.

| Medicament | Sterilising condition | Mean $Log_{10}$ Count/ml Sample Time (mins) | |
|---|---|---|---|
| | | 0 | 5 |
| None (Control) | | 5.78 ± 0.01 | 5.80 ± 0.02 |
| Un-milled | Non-Sterile | 5.89 ± 0.07 | 2.12 ± 0.05 |
| Milled | | 5.83 ± 0.03 | 2.09 ± 0.53 |
| None (Control) | | 5.93 ± 0.08 | 5.88 ± 0.06 |
| Un-milled | | 5.90 ± 0.10 | 2.18 ± 0.80 |
| Milled | | 5.76 ± 0.18 | 2.77 ± 0.01 |

I claim:

1. An adhesive composition, suitable for medical applications, comprising an adhesive having dispersed therein 2–10% by weight, based on the weight of the composition, of solid particles of chlorhexidine gluconate, wherein said particles have a particle size of less than 125 μm and at least about 30% by volume of the particles have a particle size of not less than 5 μm.

2. A composition as claimed in claim 1 wherein the adhesive is an acrylic or polyvinyl ether based adhesive.

3. An adhesive product comprising a backing layer having coated thereon an adhesive composition as defined in any one of the preceding claims.

4. A product as claimed in claim 3 which has a moisture vapor transmission rate of at least 300 $gm^{-2}$ $24h^{-1}$ at 37° C. and at a 100% to 10% relative humidity difference when in contact with moisture vapor.

5. A product as claimed in claim 3 in which the backing layer is a flexible material selected from knitted, woven or non-woven fabrics, nets, microporous or continuous synthetic polymer films.

6. A product as claimed in claim 5 wherein the backing layer is a synthetic polymer film comprising a polyurethane.

7. A product as claimed in claim 6 wherein the polyurethane comprises a hydrophilic polyurethane which contains from 5 to 50% by weight of water when hydrated.

8. A product as claimed in any of the claims 4 to 7 in the form of a wound dressing for non-exuding wounds and having an adhesive thickness of up to about 5 mm.

9. A product as claimed in any one of the claims 4 to 7 in the form of a wound dressing for exuding wounds and having an adhesive thickness of up to 25 mm.

10. A dressing pack containing a dressing as claimed in claim 9 in sterile form and contained within a bacteria and water proof pouch.

11. A method of treating a wound on an animal by applying to the wound an adhesive dressing as claimed in claim 9.

* * * * *